United States Patent
Chen et al.

(10) Patent No.: US 11,122,352 B2
(45) Date of Patent: Sep. 14, 2021

(54) WIRELESS EARPHONE

(71) Applicant: GOERTEK INC., Weifang (CN)

(72) Inventors: Shuang Chen, Weifang (CN); Yuge Zhu, Weifang (CN); Tianrong Dai, Weifang (CN); Hongmei Wang, Weifang (CN); Lin Qi, Weifang (CN)

(73) Assignee: GOERTEK INC., Weifang (CN)

( * ) Notice: Subject to any disclaimer, the term of this patent is extended or adjusted under 35 U.S.C. 154(b) by 14 days.

(21) Appl. No.: 16/622,238

(22) PCT Filed: May 20, 2019

(86) PCT No.: PCT/CN2019/087587
§ 371 (c)(1),
(2) Date: Dec. 12, 2019

(87) PCT Pub. No.: WO2019/233265
PCT Pub. Date: Dec. 12, 2019

(65) Prior Publication Data
US 2020/0107103 A1    Apr. 2, 2020

(30) Foreign Application Priority Data

Jun. 5, 2018 (CN) .......................... 201820873231.7

(51) Int. Cl.
*H04R 5/04* (2006.01)
*H04R 1/10* (2006.01)
*A61B 5/00* (2006.01)

(52) U.S. Cl.
CPC ......... *H04R 1/1016* (2013.01); *A61B 5/6817* (2013.01); *A61B 5/6843* (2013.01); *H04R 1/1041* (2013.01); *H04R 1/1083* (2013.01)

(58) Field of Classification Search
CPC .. A61B 5/6817; A61B 5/6843; H04M 1/6066; H04R 1/1016; H04R 1/1041; H04R 1/1083; H04R 5/04; H04S 1/005
(Continued)

(56) References Cited

U.S. PATENT DOCUMENTS

| 9,866,966 B2 * | 1/2018 | Lott .................... H04S 1/005 |
| 2005/0058313 A1 * | 3/2005 | Victorian ............ H04R 25/558 |
| | | 381/315 |

(Continued)

FOREIGN PATENT DOCUMENTS

| CN | 103297889 A | 9/2013 |
| CN | 107852541 A | 3/2018 |

(Continued)

OTHER PUBLICATIONS

Written Opinion of the International Search Report corresponding to International Application No. PCT/CN2019/087587, dated Aug. 8, 2019 (with English Translation).

*Primary Examiner* — Gerald Gauthier
(74) *Attorney, Agent, or Firm* — Arent Fox LLP

(57) ABSTRACT

A wireless earphone comprising an in-ear portion which is in contact with a human ear when the wireless earphone is worn. The in-ear portion comprises a wearing surface which couples the human ear canal when the wireless earphone is worn. The in-ear portion is provided with a wearing detection sensor, a sound venting hole and a contact group which are all disposed on the wearing surface. The wearing detection sensor, the sound venting hole and the contact group are all disposed on the wearing surface of the in-ear portion coupling the human ear canal, so that the wearing detection sensor can directly contact the skin of the human body when the earphone is worn, and thus the wearing detection sensor is improved.

9 Claims, 2 Drawing Sheets

(58) Field of Classification Search
USPC ........ 315/307; 381/74, 150, 309, 17, 57, 58,
381/60, 67, 71.6, 110, 123, 158, 313,
381/314, 315, 327, 334, 380; 600/476;
701/428
See application file for complete search history.

(56) References Cited

U.S. PATENT DOCUMENTS

| | | | | |
|---|---|---|---|---|
| 2010/0020998 | A1* | 1/2010 | Brown | H04R 1/1041 381/380 |
| 2011/0012534 | A1* | 1/2011 | West | F21V 23/0492 315/307 |
| 2011/0051977 | A1* | 3/2011 | Losko | H04R 25/55 381/380 |
| 2011/0081037 | A1* | 4/2011 | Oh | A61B 5/6898 381/380 |
| 2013/0279724 | A1* | 10/2013 | Stafford | H04R 5/04 381/309 |
| 2014/0037101 | A1* | 2/2014 | Murata | H04R 1/1041 381/74 |
| 2014/0086438 | A1* | 3/2014 | Tachibana | H04R 1/1091 381/309 |
| 2014/0348365 | A1* | 11/2014 | Edwards | G02C 11/10 381/327 |
| 2014/0348367 | A1* | 11/2014 | Vavrus | H04R 1/44 381/334 |
| 2014/0355791 | A1 | 12/2014 | Tang | |
| 2014/0369537 | A1* | 12/2014 | Pontoppidan | H04R 25/505 381/314 |
| 2015/0215701 | A1* | 7/2015 | Usher | H04R 1/1041 381/71.6 |
| 2015/0281824 | A1* | 10/2015 | Nguyen | H04R 1/1041 381/74 |
| 2015/0326969 | A1* | 11/2015 | Tu | H04R 1/1041 381/74 |
| 2015/0366475 | A1* | 12/2015 | Just | A61B 5/02416 600/476 |
| 2016/0014539 | A1* | 1/2016 | Yeh | H04R 5/033 381/309 |
| 2016/0037249 | A1* | 2/2016 | Kumar | H04R 1/105 381/74 |
| 2016/0073188 | A1* | 3/2016 | Linden | H04R 1/1025 381/309 |
| 2016/0080855 | A1* | 3/2016 | Greenberg | H04R 1/04 381/74 |
| 2017/0034615 | A1 | 2/2017 | Mankodi et al. | |
| 2017/0094389 | A1* | 3/2017 | Saulsbury | A61B 5/6817 |
| 2017/0094399 | A1* | 3/2017 | Chandramohan | A45C 13/005 |
| 2017/0230754 | A1* | 8/2017 | Dusan | H04R 1/1016 |
| 2017/0238087 | A1* | 8/2017 | Chawan | H04R 5/033 381/380 |
| 2017/0289668 | A1* | 10/2017 | Kim | H04R 1/1041 |
| 2019/0052951 | A1* | 2/2019 | Kofman | H04R 1/1041 |
| 2020/0107103 | A1* | 4/2020 | Chen | H04R 1/1083 |

FOREIGN PATENT DOCUMENTS

| | | |
|---|---|---|
| CN | 208434085 U | 1/2019 |
| WO | 2017183027 A1 | 10/2017 |

* cited by examiner

WIRELESS EARPHONE

CROSS REFERENCE TO RELATED APPLICATIONS

This application is a U.S. National Stage entry under 35 U.S.C. § 371 based on International Application No. PCT/CN2019/087587, filed on May 20, 2019, which claims priority to Chinese Patent Application No. 201820873231.7, filed on Jun. 5, 2018. The embodiment of the priority applications are hereby incorporated herein in their entirety by reference.

TECHNICAL FIELD

The present disclosure relates to the technical field of earphones, and in particular, to a wireless earphone.

BACKGROUND

The wireless earphone is free from the constraint of the earphone cable and makes it more comfortable and convenient to wear. Some wireless earphones are also additionally provided with a wearing detection device and the like, but in the conventional wireless earphones, the spatial position design of the wearing detection device and the like is unreasonable, resulting in the space of the main board being occupied; moreover, the wearing detection effect is not satisfactory, and the detection result is not accurate enough.

SUMMARY

In view of the problem of the wireless earphones in the prior art that the spatial position of the wearing detection device and the like is unreasonable, the present disclosure proposes a wireless earphone in order to solve the above problem or at least partially solve the above problem.

In order to achieve the above object, the present disclosure adopts the following technical solutions:

A wireless earphone comprising an in-ear portion which is in contact with a human ear when the wireless earphone is worn, wherein the in-ear portion comprises a wearing surface which couples the human ear canal when the wireless earphone is worn;

the in-ear portion is provided with a wearing detection sensor, a sound venting hole and a contact group which are all disposed on the wearing surface.

Optionally, the contact group comprises a charging contact for connecting a charging device to charge the wireless earphone, and a communication contact for connecting the charging device and performing information transmission.

Optionally, the wireless earphone is further provided therein with an acceleration sensor, the acceleration sensor and the wearing detection sensor are connected respectively to a controller in the wireless earphone, and the controller receives detection signals of the acceleration sensor and the wearing detection sensor and uses them in wearing detection.

Optionally, a sound emitting hole is provided on a side of the in-ear portion, and the sound venting hole is disposed at a side of the wearing surface which is close to the sound emitting hole.

Optionally, the wearing detection sensor is disposed at a position near the center of the wearing surface, and the contact group is disposed at a side of the wearing detection sensor which is far from the sound venting hole.

Optionally, the wireless earphone further comprises a middle frame portion and a rear casing portion; the casings of the in-ear portion, the middle frame portion, and the rear case portion are connected together to form an outer casing of the wireless earphone; a curved transition region which is curved inward is provided at the boundary between the front end of the middle frame portion and the in-ear portion; the diameter of the middle frame portion gradually increases rearward, and the cross-sectional area of the rear end of the middle frame portion is larger than the maximum cross-sectional area of the in-ear portion; and the rear casing portion has a flat truncated cone shape and covers the rear end of the middle frame portion.

Optionally, a surface of the rear case portion is provided with a capacitive touch panel.

Optionally, the wireless earphone is further provided therein with a battery, a controller and a Bluetooth chip.

Optionally, the contact group uses Pogopin probes, and comprises two charging contact Pogopin probes and one communication contact Pogopin probe, and the communication contact Pogopin probe is connected to the Bluetooth chip through circuits inside the wireless earphone to transmit information.

Optionally, the wireless earphone further comprises a calling microphone and a noise reduction microphone.

In sum, the beneficial effects of the present disclosure are as follows.

The wearing detection sensor, the sound venting hole and the contact group are all disposed on the wearing surface of the in-ear portion coupling the human ear canal, so that the wearing detection sensor can directly contact the skin of the human body when the earphone is worn, and thus the detection accuracy of the wearing detection sensor is improved. In addition, the sound venting hole is located on the wearing surface of the in-ear portion, and the sound can be released to the human ear, and thus the sound quality is improved. Moreover, since the wearing surface is generally flat, it is easy to mount the wearing detection sensor, the sound venting hole and the contacts on the wearing surface, and it is also convenient to align the accessories such as the charging box by the wearing surface, and thus good contact of the contact group is achieved.

1: contact group; 2: wearing detection sensor; 3: sound venting hole; 4: sound emitting hole; 5: in-ear portion; 6: middle frame portion; 61: curved transition region; 7: rear case portion; 8: noise reduction microphone hole; and 9: calling microphone hole.

DETAILED DESCRIPTION

In order to make the objects, technical solutions and advantages of the present disclosure clearer, the embodiments of the present disclosure will be further described in detail below with reference to the accompanying drawings.

The technical idea of the present disclosure is to more reasonably design the spatial position of the wearing detection sensor and the like in the wireless earphone, and to improve the wearing detection accuracy of the wireless earphone. When the wearing detection sensor, the sound venting hole and the contact group are all disposed on the wearing surface of the in-ear portion coupling the human ear canal, the wearing detection sensor can directly contact the skin of the human body when the earphone is worn, and thus detection accuracy of the wearing detection sensor is improved. In addition, the sound venting hole is located on the wearing surface of the in-ear portion, and the sound can be released to the human ear, and thus the sound quality is improved. Moreover, since the wearing surface is generally flat, it is easy to mount the wearing detection sensor, the sound venting hole and the contact group on the wearing surface, and it is also convenient to align the accessories such as the charging box by the wearing surface, and thus good contact of the contact group is achieved.

Figure 1:
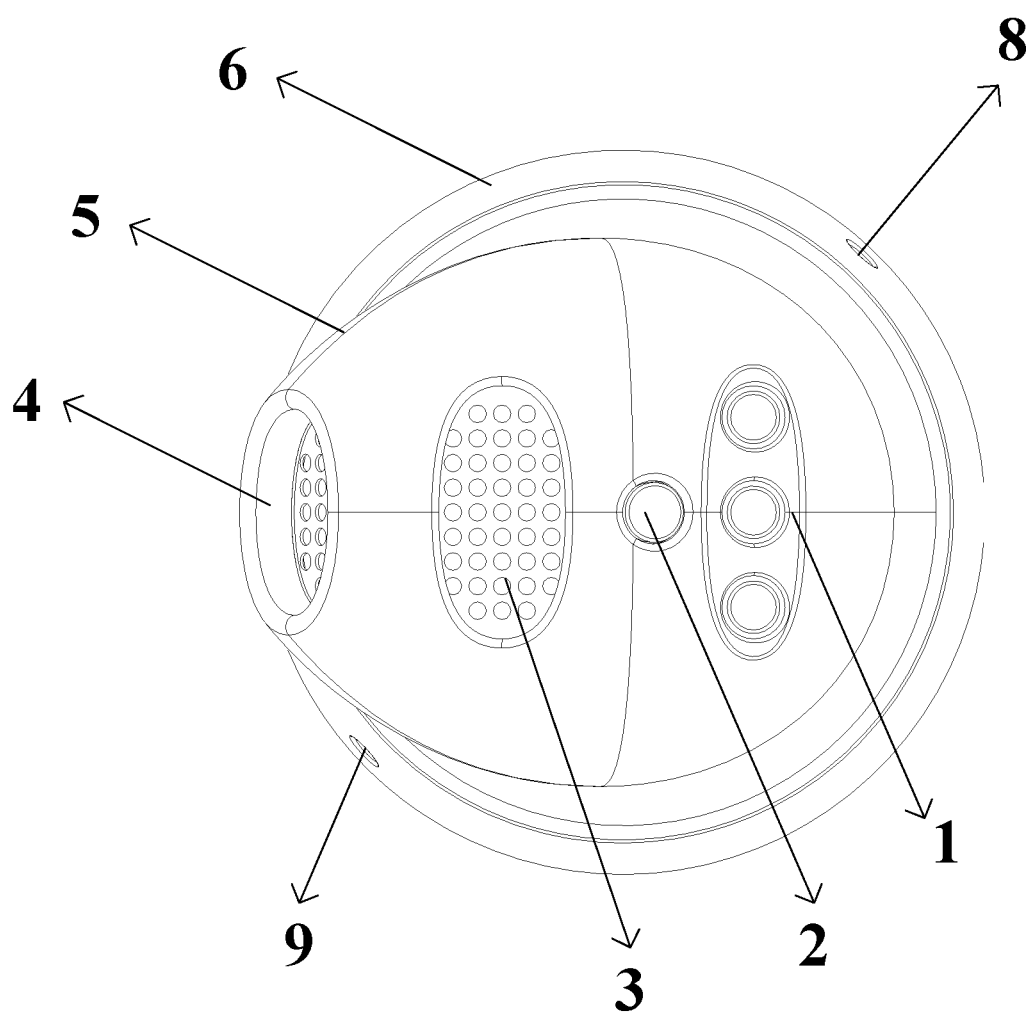
FIG. 1 is a schematic view of a wireless earphone in accordance with an embodiment of the present disclosure when facing a wearing surface of an in-ear portion.
Figure 2:
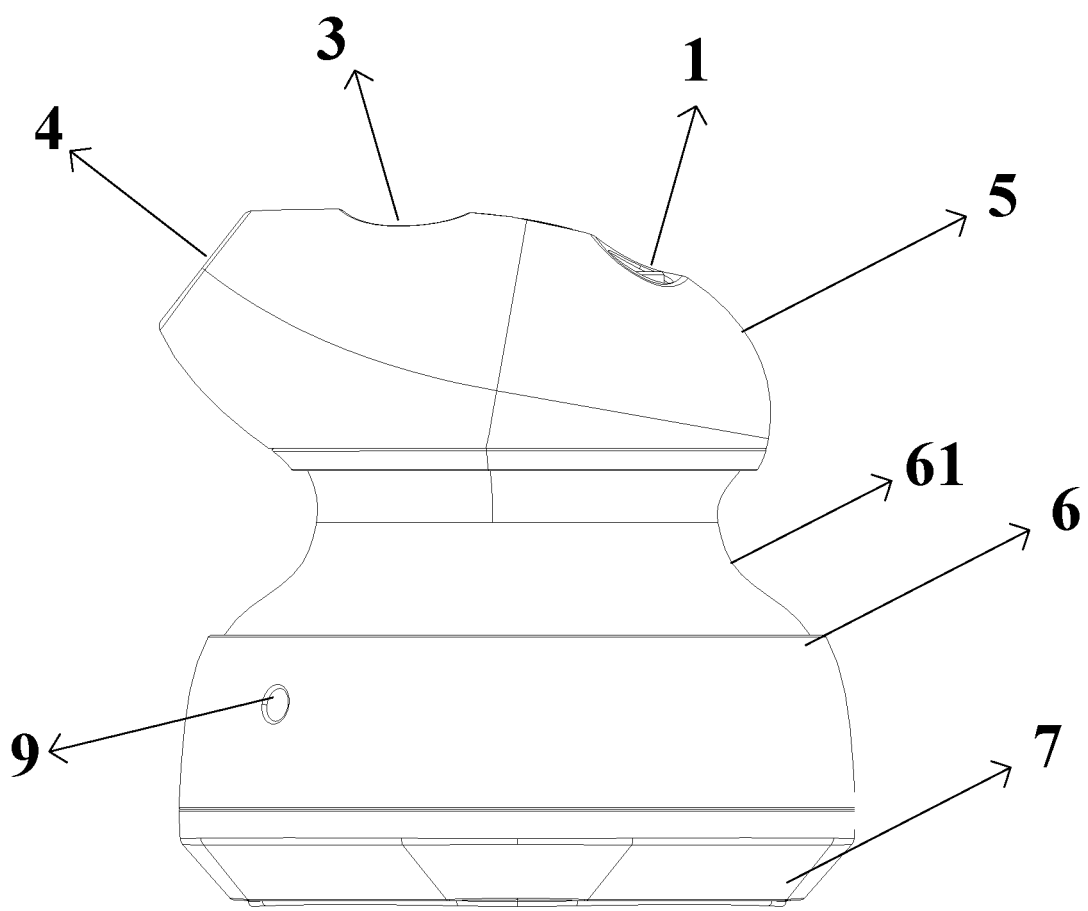
FIG. 2 is a schematic side view of a wireless earphone in accordance with an embodiment of the present disclosure.

FIG. 1 is a schematic view of a wireless earphone in accordance with an embodiment of the present disclosure when facing the wearing surface of an in-ear portion, and FIG. 2 is a schematic side view of a wireless earphone in accordance with an embodiment of the present disclosure.

Referring to FIG. 1, in an exemplary embodiment of the wireless earphone, the wireless earphone includes an in-ear portion 5 and the in-ear portion 5 contacts the human ear when the wireless earphone is worn. The in-ear portion 5 comprises a wearing surface, which is the front side of the wireless earphone shown in FIG. 1 and faces outside of the paper. The wearing surface couples the human ear canal when the wireless earphone is worn. The in-ear portion 5 is provided with a wearing detection sensor 2, a sound venting hole 3 and a contact group 1, and the wearing detection sensor 2, the sound venting hole 3 and the contact group 1 are all disposed on the wearing surface.

During the use of the wireless earphone, there are problems such as that the wireless earphone falls out and the wearing position cannot achieve good sound effects. Therefore, it is necessary to detect the wearing condition of the wireless earphone. However, in the conventional wireless earphone design, the wearing detection sensor is usually disposed in the inner space of the middle frame portion of the wireless earphone, and thus occupies the space of the main board and affects the casing design of the wireless earphone; moreover, there is a problem of insensitivity when the wearing detection sensor is in the middle frame.

Accordingly, in the present disclosure, by disposing all of the wearing detection sensor, the sound venting hole and the contact group on the wearing surface of the in-ear portion, the wearing surface coupling the human ear canal, the wearing detection sensor can directly contact the skin of the human body when the earphone is worn, and thus detection accuracy of the wearing detection sensor is improved. In addition, the sound venting hole is located on the wearing surface of the in-ear portion, and the sound can be released to the human ear, and thus the sound quality is improved. Moreover, since the wearing surface is generally flat, it is easy to mount the wearing detection sensor, the sound venting hole and the contacts on the wearing surface, and it is also convenient to align the accessories such as the charging box by the wearing surface, and thus good contact of the contact group is achieved.

The sounding unit, the wearing detection sensor 2 and the contact group 1 of the wireless earphone can be connected together by a same flexible circuit board and extend downward to connect the main board in the middle frame.

In an embodiment of the present disclosure, the wireless earphone may be a Bluetooth earphone connected to a terminal device, such as a True Wireless Stereo (TWS) earphone, or a wireless earphone with a storage function and capable of playing music independently.

The wireless earphone is free from the constraint of the earphone cable, and is connected to the charging box through the contact group on the wireless earphone to realize the charging function and the like. In an embodiment of the present disclosure, the contact group 1 comprises a charging contact for connecting a charging device to charge the wireless earphone, and a communication contact for connecting the charging device and performing information transmission, thereby not only realizing the charging of the wireless earphone, but also realizing the communication between the wireless earphone and the charging device to achieve the preset command and function and the like.

As an example, in the embodiment of the present disclosure shown in FIG. 1 and FIG. 2, the wireless earphone is further provided therein with a battery, a controller and a Bluetooth chip, that is, the wireless earphone is a Bluetooth wireless earphone connected wirelessly through Bluetooth.

On this basis, referring to FIG. 1, the contact group 1 uses Pogopin probes, and comprises two charging contact Pogopin probes and one communication contact Pogopin probe. Two charging contact Pogopin probes are connected respectively to the positive and negative charging terminals of the battery, and receive the charging of the wireless earphone from the charging device. The communication contact Pogopin probe is connected to the Bluetooth chip through the circuits inside the wireless earphone to transmit information. For example, the communication contact Pogopin probe can transmit different information by transmitting different voltage values, and the wireless earphone wirelessly transmits the received information to the data terminal connected to the wireless earphone using the Bluetooth chip, and realizes different functions correspondingly.

Therefore, when the wireless earphone is connected to a matching charging box, the three Pogopin probes are in contact with the corresponding contacts of the charging box, thereby realizing charging of the wireless earphone and obtaining information and instructions transmitted from the charging box through the communication contact, and the information and instructions are further sent to a terminal connected to the wireless earphone, such as a mobile phone, through the Bluetooth chip of the wireless earphone. In this way, the charging box can realize information communication with the terminal by aid of the wireless earphone, thereby saving the cost of providing a separate communication device in the charging box.

In order to improve the accuracy of the wearing detection of the wireless earphone, in an embodiment of the present disclosure, the wireless earphone is further provided therein with an acceleration sensor. The acceleration sensor and the wearing detection sensor 2 are connected respectively to a controller in the wireless earphone, and the controller receives the detection signals of the acceleration sensor and the wearing detection sensor 2 and uses them in wearing detection.

Since the acceleration sensor can detect the movement of the earphone, combined with a static detection of the wearing distance of the earphone and the like by the wearing detection sensor 2, it can be better judged whether the user wears the earphone, so that the accuracy of the wearing detection is higher. In the embodiment shown in FIG. 1 and FIG. 2, the wearing detection sensor 2 is an infrared wearing detection sensor which is a mature sensor currently used and has a satisfactory wearing detection effect. In addition, the acceleration sensor provided in the wireless earphone can also work separately, for example, to collect the user's motion information, realize a step counting function, and the like.

As an audio playback device, the sound quality is an extremely important indicator in the design of wireless earphones. In order to improve the sound quality of the wireless earphone, as shown in FIG. 1, in an embodiment of the present disclosure, a sound emitting hole 4 is provided on a side of the in-ear portion 5, and the sound venting hole 3 is disposed on a side of the wearing surface, the side being close to the sound emitting hole 4. When the sound venting hole 3 and the sound emitting hole 4 are arranged close to each other, the sound pressure of the sound emitting position can be released, and the sound releasing hole 3 and the sound emitting hole 4 are simultaneously close to the human ear canal outlet, which is beneficial to improve the sound quality and effect heard by the human ear when wearing the earphone.

The space on the wearing surface of the wireless earphone must be properly divided and used. In an embodiment of the present disclosure, as shown in FIG. 1, the sound venting hole 3 and the sound emitting hole 4 are disposed close to each other so as to ensure good sound quality; the wearing detection sensor 2 is disposed at a position near the center of the wearing surface so as to ensure the contact with the human ear, and the wearing detection is performed more accurately. The contact group 1 is disposed on aside of the wearing detection sensor 2, the side being far from the sound venting hole 3, to make full use of the space, maintain reasonable distances among the components and align with the contacts of the matching charging box.

Besides the sound quality, the structure and shape design of wireless earphones is also important. In an embodiment of the present disclosure, as shown in FIG. 2, the wireless earphone further comprises a middle frame portion 6 and a rear casing portion 7, so that the casings of the in-ear portion 5, the middle frame portion 6, and the rear case portion 7 are connected together to form an outer casing of the wireless earphone. A curved transition region 61 that is curved inward is provided at the boundary between the front end of the middle frame portion 6 and the in-ear portion 5. The curved transition region 61 is curved inward to make the rear portion of the in-ear portion 5 of the wireless earphone to be thinner, which can avoid squeezing the auricle cartilage and facilitate the in-ear portion 5 inserting into the auricle cartilage, so that the earphone is comfortably and firmly worn on the human ear canal. In addition, the diameter of the middle frame portion 6 gradually increases rearward, and the cross-sectional area of the rear end of the middle frame portion 6 is larger than the maximum cross-sectional area of the in-ear portion 5, that is, the middle frame portion 6 is thicker than the in-ear portion 5, which is convenient for the user to operate manually, and at the same time, provides a larger inner space for disposing the components of the wireless earphone, such as the main board and battery. Finally, the rear casing portion 7 has a flat truncated cone shape and covers the rear end of the middle frame portion 6, which is aesthetically pleasing and has no sharp edges and corners.

In an embodiment of the present disclosure, the surface of the rear casing portion 7 is further provided with a capacitive touch panel. The capacitive touch panel is used as a user's input control device for realizing functions such as control of tuning. The capacitive touch panel can be connected to the internal circuit of the wireless earphone through a structure such as a Pogopin on the main board.

In an embodiment of the present disclosure, the wireless earphone further has a calling function, and comprises a calling microphone and a noise reduction microphone, thereby achieving a calling function and a noise reduction function. The noise reduction microphone and the calling microphone can be disposed in the middle frame through the flexible circuit board. The sound is collected through a noise reduction microphone hole 8 and a calling microphone hole 9 on the middle frame, as shown in FIG. 1.

The above description is merely specific embodiments of the present disclosure. Based on the above teachings of the present disclosure, those skilled in the art may make other improvements or modifications on the basis of the foregoing embodiments. It should be understood by those skilled in the art that the above specific description is only for better explaining the present disclosure, and the scope of the present disclosure should be defined by the protection scope of the claims.

What is claimed is:

1. A wireless earphone, comprising an in-ear portion which is in contact with a human ear when the wireless earphone is worn, wherein
   the in-ear portion comprises a wearing surface which couples an human ear canal when the wireless earphone is worn, wherein the wearing surface is flat;
   the in-ear portion is provided with a wearing detection sensor, a sound venting hole and a contact group which are all disposed on the wearing surface;
   wherein the wearing detection sensor, the sound venting hole and the contact group are all disposed on the flat wearing surface which can directly contact skin of a human body when the earphone is worn;
   wherein the wearing detection sensor is disposed at a position near the center of the wearing surface, and the contact group is disposed on a side of the wearing detection sensor to be spaced apart from the sound venting hole.

2. The wireless earphone according to claim 1, wherein the contact group comprises a charging contact for connecting a charging device to charge the wireless earphone, and a communication contact for connecting the charging device and performing information transmission.

3. The wireless earphone according to claim 1, wherein the wireless earphone is further provided therein with an acceleration sensor, the acceleration sensor and the wearing detection sensor are connected respectively to a controller in the wireless earphone, and the controller receives detection signals of the acceleration sensor and the wearing detection sensor and uses them in wearing detection.

4. The wireless earphone according to claim 1, wherein a sound emitting hole is provided on a side of the in-ear portion, and the sound venting hole is disposed on a side of the wearing surface which is close to the sound emitting hole.

5. The wireless earphone according to claim 1, wherein the wireless earphone further comprises a middle frame portion and a rear casing portion;
   the casings of the in-ear portion, the middle frame portion, and the rear case portion are connected together to form an outer casing of the wireless earphone;
   a curved transition region which is curved inward is provided at the boundary between a front end of the middle frame portion and the in-ear portion;
   the diameter of the middle frame portion gradually increases rearward, and the cross-sectional area of the rear end of the middle frame portion is larger than the maximum cross-sectional area of the in-ear portion; and the rear casing portion has a flat truncated cone shape and covers the rear end of the middle frame portion.

6. The wireless earphone according to claim 5, wherein a surface of the rear case portion is provided with a capacitive touch panel.

7. The wireless earphone according to claim 2, wherein the wireless earphone is further provided therein with a battery, a controller and a Bluetooth chip.

8. The wireless earphone according to claim 7, wherein the contact group uses Pogopin probes, and comprises two charging contact Pogopin probes and one communication contact Pogopin probe, and the communication contact Pogopin probe is connected to the Bluetooth chip through circuits inside the wireless earphone to transmit information.

9. The wireless earphone according to claim 1, wherein the wireless earphone further comprises a calling microphone and a noise reduction microphone.

* * * * *